United States Patent [19]
Collinsworth

[11] Patent Number: 5,895,403
[45] Date of Patent: Apr. 20, 1999

[54] SURGICAL CUTTING TOOL

[76] Inventor: Lonnie Rae Collinsworth, 1722 S. Carson, Suite 1905, Tulsa, Okla. 74119

[21] Appl. No.: 08/953,608

[22] Filed: Oct. 17, 1997

[51] Int. Cl.⁶ .................................................. A61B 17/16
[52] U.S. Cl. ......................... 606/184; 606/185; 606/187
[58] Field of Search ................................ 606/184, 185, 606/186, 187, 131, 133, 167

[56] References Cited

U.S. PATENT DOCUMENTS

| | | |
|---|---|---|
| 3,867,942 | 2/1975 | Bellantoni et al. |
| 3,995,619 | 12/1976 | Glatzer |
| 4,476,864 | 10/1984 | Tezel |
| 4,705,038 | 11/1987 | Sjostrom et al. |
| 5,012,797 | 5/1991 | Liang et al. ........................ 606/131 |
| 5,036,860 | 8/1991 | Leigh et al. |
| 5,133,360 | 7/1992 | Spears |
| 5,172,702 | 12/1992 | Leigh et al. |
| 5,322,505 | 6/1994 | Krause et al. |
| 5,403,317 | 4/1995 | Bonutti |
| 5,405,348 | 4/1995 | Anspach, Jr. et al. |
| 5,578,054 | 11/1996 | Arnold ................................. 606/184 |
| 5,611,810 | 3/1997 | Arnold et al. ....................... 606/187 |

FOREIGN PATENT DOCUMENTS

WO 94/07433  4/1994  France.

Primary Examiner—Michael Buiz
Assistant Examiner—Kevin Truong
Attorney, Agent, or Firm—Head, Johnson & Kachigian

[57] ABSTRACT

A surgical cutting tool having a "stepped" or "funneled" axial passageway for the evacuation of tissue plugs. The tool is made of a length of cylindrical surgical steel having an axial bore therethrough. The proximal end of the tool terminates in a cutting tip which has a cutting edge sufficient to cut tissue plugs of a desired diameter. The distal end is adapted for connection to a vacuum source. The axial bore has a first inside diameter at the cutting edge, a second inside diameter greater than the first inside diameter forming a first relief near the cutting edge, and a third inside diameter greater than the second inside diameter forming a second relief upstream of the first relief. This funnel configuration from the proximal end to the distal end of the tool allows tissue plugs to be easily evacuated from the tool.

12 Claims, 1 Drawing Sheet

SURGICAL CUTTING TOOL

BACKGROUND OF THE INVENTION

1. Technical Field

This invention relates generally to surgical cutting instruments, and, more specifically, to a surgical cutting tool having a vacuum clearance capability for use in connection with rotary cutting instruments in the field of hair transplantation.

2. Background

Many people experience over time a gradual thinning of hair with age. Men in particular are prone to receding hairlines and the loss of hair from the crown of the head, so-called male pattern baldness. Many men and women suffering from hair loss turn to hairpieces or wigs in an effort to retain a youthful appearance.

Those wanting a more permanent solution to hair loss have undergone conventional treatments for hair restoration. Preparations containing minoxidil have been shown to be effective, particularly in younger persons, but they must be applied twice a day and use must be continued indefinitely as hair loss will recur if the application is stopped. In some users minoxidil causes skin irritation.

Though hormone therapy has been prescribed for certain types of hair loss, as with other hormone treatments it is not without risk.

In an effort to achieve more significant results, hair transplantation has become an important treatment for hair loss. It involves the relocation of plugs of skin from parts of the scalp containing active hair follicles to bald areas. The process includes preparing a "recipient site," i.e. that portion of the scalp where a skin plug is removed, in the bald areas and transplanting an active hair follicle into the recipient site.

Another procedure, termed scalp reduction, may also utilize hair follicle transplantation. In scalp reduction the scalp is tightened so that hair bearing skin from the back and sides of the head is pulled toward the crown. Hair may then be transplanted to the remaining bald area at the top of the head.

Heretofore the most common method to prepare recipient sites for hair follicle transplantation has been to stab the scalp with a non-cannulated biopsy type punch for the purpose of removing cylindrical tissue plugs. This type of cutting instrument has a tubular design at the cutting tip and employs a vent hole in its side to facilitate removal of small plugs from the scalp by relieving pressure build-up. The punch, once filled with plugs, is generally handed to an assistant who must clean out the punch of plugs removed. As can be imagined, this is a laborious and offensive task. The surgeon continues the process with another clean punch.

Recent attempts have been made to somewhat automate the hair transplantation process. Certain punches have been modified with a steel shank to fit into the chuck of a motor driven power source, such as a dentist's drill, to make preparation of recipient sites easier. Other systems have been developed to more completely automate the entire process of hair transplantation. These systems utilize a surgical cutting tool coupled to a vacuum source designed to cut tissue plugs and remove them by suction.

Examples of conventional surgical instruments and systems are described in U.S. Pat. Nos. 3,867,942; 4,476,864; 5,133,360; 5,172,702; 5,403,317 and PCT International Publication WO 94/07433.

One drawback to existing systems, particularly those attempting to utilize vacuum pressure for tissue plug evacuation, is the tendency of cutting tools to clog with debris. It has been found difficult to provide rotary cutting systems utilizing vacuum suction to evacuate tissue plugs from the cutting instrument which do not have this tendency.

It is therefore an object of the present invention to provide a cutting tool having vacuum clearance capability which can be used either manually or in rotary instruments and which can more effectively evacuate tissue plugs cut from the scalp.

It is another object of the present invention to provide the surgeon a single cutting instrument that can be used to complete work in the entire recipient area without a tiresome exchange of instruments.

It is a further object of the present invention to provide a method of making such a surgical cutting instrument that provides for new various sizes of cutting tips.

SUMMARY OF THE INVENTION

These and other objects and advantages are achieved in a surgical cutting tool having a "stepped" or "funneled" axial passageway for the evacuation of tissue plugs. The tool is made of a length of cylindrical surgical steel having an axial bore therethrough. The proximal end of the tool terminates in a cutting tip which has a cutting edge to cut tissue plugs of a desired diameter. The distal end of the tool is adapted to connect to a vacuum source. The axial bore has a first inside diameter at the cutting edge, a second inside diameter greater than the first inside diameter forming a first relief near the cutting edge, and a third inside diameter greater than the second inside diameter forming a second relief upstream of the first relief. This funnel configuration from the proximal end to the distal end of the tool allows tissue plugs to be easily evacuated from the tool. As vacuum is applied at the distal end of the tool the tissue plugs cut at the cutting edge pass easily through the first and second reliefs to exit the axial bore. The cutting tool is preferably utilized in a chuck of a rotary surgical instrument connected to a motor driven power source. Alternatively, the tool may be manually operated.

The surgical cutting tool is made by first cutting a piece a cylindrical surgical steel to a desired length to obtain a blank. A drill hole is made at one end (corresponding to the proximal end) of the blank to form the cutting edge. The other end (corresponding to the distal end) of the blank is drilled open along its entire longitudinal axis with a first bit so as to create the axial bore therethrough. A first step-back cut is made from the distal end of the blank toward the proximal end with a second bit having a diameter greater than the first bit to form the first relief. A second step-back cut is then made from the distal end toward the proximal end with a third bit having a diameter greater than the second bit to form the second relief. A cutting tip is ground onto the proximal end of the tool and the axial bore is polished to a smooth finish to further facilitate the evacuation of tissue plugs.

A better understanding of the invention and its objects and advantages will become apparent to those skilled in this art from the following detailed description, taken in conjunction with the attached drawings, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature and not as restrictive.

DETAILED DESCRIPTION OF THE PREFERRED EMBODIMENT

Figure 3:
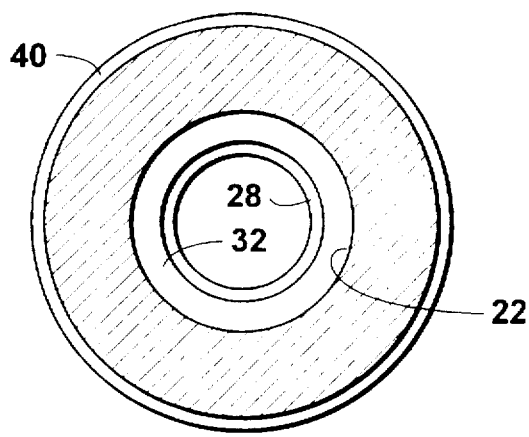
FIG. 3 is a cross-sectional view taken along line 3—3 of FIG. 1.

Referring to the drawings, the preferred cutting tool is generally indicated by the reference numeral 10. The cutting tool is preferably made of a length of cylindrical surgical steel such as hardened 420 stainless steel. The tool 10 has a proximal end 12 and a distal end 14. Formed at the proximal end 12 of the tool 10 is a conical cutting tip 16. In the most preferred embodiment the cutting tip 16 is angled (20 degrees) from the point of angle 18 toward the longitudinal axis of the tool. The cutting tip 16 terminates in a cutting edge 20.

Figure 2:
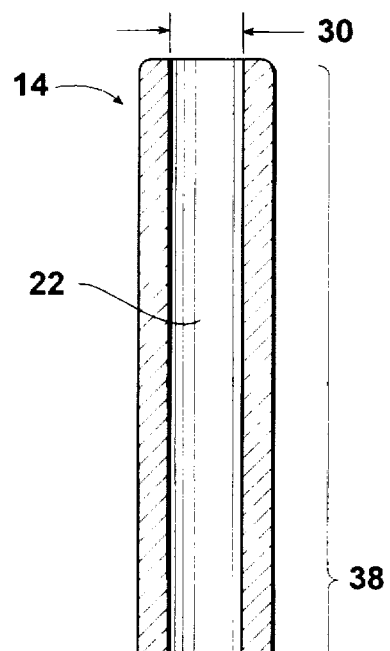
FIG. 2 is a cross-sectional view taken along line 2—2 of FIG. 1.
Figure 1:
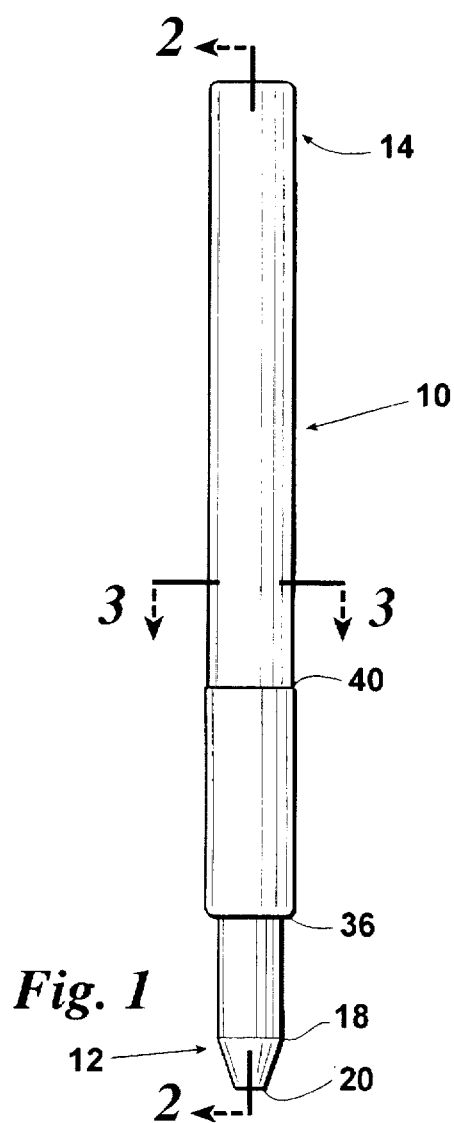
FIG. 1 is a elevational view of the preferred surgical cutting tool.

An axial bore 22 is formed longitudinally through the length of the tool 10. The axial bore 22 has a first inside diameter 24 at the cutting edge 20. The diameter of the axial bore 22 expands to a second inside diameter 26 which is greater than the first inside diameter 24 at a point distal to but near the cutting edge 20, thereby forming a first relief 28. Best seen in FIG. 2, the first relief 28 lies with the point of angle 18 in an imaginary plane cut transverse to the longitudinal axis of the tool 10. The axial bore 22 has a further third inside diameter 30 which is greater than the second inside diameter 26 and which forms a second relief 32 upstream or distal to the first relief 28. Thus, it can be seen that as vacuum is applied to the distal end 14 of the tool 10, and as the tool is pressed to the scalp and rotated to generate tissue plugs, the plugs cut at the cutting edge 20 are evacuated through the axial bore 22 passing first through the first relief 28 and subsequently through the second relief 32. It has been found that this construction of the axial bore 22 allows for the efficient evacuation of tissue plugs through the tool 10 and eliminates typical clogging problems.

In the most preferred embodiment the tool is approximately 1.50 inches (3.81 cm) in length. The first inside diameter 24 at the cutting edge 20 can be made to be between 0.0020 inches (0.05 mm) and 0.0600 inches (1.50 mm). In the most preferred embodiment the first inside diameter is approximately 0.0394 inches (1 mm). In this most preferred embodiment the second inside diameter 26 is approximately 0.043 inches (1.1 mm), and the third inside diameter is 0.062 inches (1.57 mm).

Also in connection with the most preferred embodiment the first relief is about 0.07 inches (1.7 mm) distal to or upstream of the cutting edge 20. The second relief 32 is preferably about 0.3 inches (7.33 mm) from the cutting edge 20.

The outside surface of the tool 10 is contoured to facilitate achieving the depth of scalp penetration desired and to fit the chuck of a rotary drilling instrument. The drawings show the tool 10 to have a reduced outside diameter area 34 from the point of angle 18 of the cutting tip 16 toward the distal end 14 of the tool 10 corresponding to a desired depth of punch. This reduced outside diameter area 34 forms a ledge 36 that will abut the scalp of the patient to prevent over penetration. It should be noted that in the most preferred embodiment the first relief 28 corresponds to the point of angle 18 of the cutting tip 16 while the second relief 32 is distal to the ledge 36 created by the reduced outside diameter area 34.

The outside surface of the tool 10 has a second reduced outside area diameter area 38 at its distal end 14 to adapt to a chuck of a motor driven surgical instrument (not shown). A stop ledge 40 marks the proximal end of the second reduced outside diameter area 38 and provides an abutting surface for the chuck.

The tool 10 is manufactured in a unique manner. A piece of surgical steel, preferably hardened 420 stainless steel, is cut to a desired length to obtain a blank. The preferred length is 1.50 inches (3.81 cm). A drill hole is made at one end (now the proximal end 12) of the blank to form the cutting edge 20. The other end (now the distal end 14) of the blank is drilled open along its entire longitudinal axis with a first bit so as to create the axial bore 22 therethrough. A first step-back cut is then made from the distal end 14 toward the proximal end 12 with a second bit having a diameter greater than the first bit to form the first relief 28. A second step-back cut is thereafter made from the distal end 14 toward the proximal end 12 with a third bit having a diameter greater than the second bit to form the second relief 32. This step-back drilling procedure, or reaming process, is designed to achieve a larger opening in the distal portion of the tool 10 than in the cutting tip 16. In the most preferred embodiment following reductions are established in each cut. The distal end 14 of the blank is initially drilled open to a depth of approximately 1.430 inches (3.63 cm) to meet the drill hole made at the proximal end 12. The first step-back cut is then made from the distal end 14 to about 1.25 inches (3.175 cm), followed by the second step-back cut to 1.2 inches (3.05 cm). This creates the funnel opening critical to the operation of the cutting process. The tissue plugs are cut away at the site and released inside the axial bore 22 to allow the vacuum to pull the plugs away from the surgical site with a clean action at one time. This achieve a critical objective in the operation which is not to leave any tissue behind which may cause a cyst in the recipient site or prevent re-growth of hair.

The next step in the procedure is to grind the tool 10 to the proper outside diameter. This is to obtain a proper fit into a selected head collet. The outside diameter can be varied to adapt to different sizes of head collets and handpieces. An outside diameter having a tolerance between 0.118/0.1175 inches has been successfully utilized.

Grinding is also used to provide the stop ledge 40 in the outside diameter of the tool. The purpose of the stop ledge 40 is to keep the tool in its proper position in the head collet and is used as a stop. The stop ledge 40 can be place wherever along the outside diameter of the tool 10 necessary for a particular head collet assembly.

The cutting tip 16 is then applied to the tool 10 to a sharp, preferably 20 degree, angle with a 8–10 micro finish or better. All angles on the tool 10 with sharp edges are then rounded off in a 0.010 curve. Lastly, the inside of the tool 10 is polished to an 8–10 micro finish or better. This allows a smooth surface inside the tool for a non-sticking wall which allows an even flow of vacuum and easy extraction of tissue plugs from the axial bore 22.

The tool 10 may be utilized manually or in conjunction with a motor powered instrument. In a manual application a handle may be fashioned to the outer surface of tool 10 and a piece of vacuum tubing attached to the distal end 14. The tubing (not shown) is connected to a vacuum source (not shown). The tool is pushed and rotated into the scalp to cut tissue plugs which are removed by the action of the vacuum.

In the most preferred embodiment the tool 10 is used in conjunction with a surgical handpiece that includes a hollow inner rotary chuck or head collet and control console (not shown). The rotary chuck or head collet attachment is a modified dental unit. It provides a chuck that is cannulated through the gearing units that drive the tool 10. The preferred chuck has a diameter designed to accept a 3.0 mm shank. The distal end of the chuck head may be provided with a small cannulated hose attachment with locking fins, which allows the vacuum tubing to be attached. The head collet is attached to a standard 16:1 gear handpiece well known in the art.

The preferred console comprises a digital electric motor that incorporates a vacuum pump and system electronics. Optional features may include a plug counter that uses the pressure of the vacuum to indicate a use as a count, a high voltage switch that will allow the unit to use both 110 and 220 current with the change of a fuse, a digital RPM read out, and on/off switch with foot control, and a digital vacuum read out. The preferred console accepts all E-type pieces and includes an autoclavable brushless motor/cable assembly.

The following manufacturers make components currently used in power surgical systems that find application in connection with the present invention. Aseptico, Inc. of Kirkland, Wash. makes a console/motor/footswitch, FDA #K882526/A, usable in connection with the present invention. BVR Areo-Precision of Rockford, Ill. makes a usable contra-angle handpiece, FDA #K934571, and high torque head, FDA #K934781.

The tool 10, handpiece and console comprise a complete hair transplantation system. The handpiece receives power from the console which also houses the vacuum pump and system electronics. Tubing, such as ⅛ inch rubber tubing, is used to connect the vacuum source to the distal end 14 of the tool 10. A trap, such as a standard I.V. drip device, can be placed between the tool 10 and the vacuum source to trap the tissue plugs or the plugs can be deposited in a collection jar for disposal while the surgeon continuously creates new recipient sites. The tube may also incorporate a sterile filter in the distal end to prevent debris or bacteria from entering the vacuum pump and causing contamination. The ends of the tubes simply snap over the connection ends of the handpiece and vacuum pump such as with a barb fitting.

It can thus be appreciated that the present invention can be utilized in conjunction with a number of head collet and handpiece assemblies and in connection with various hair transplantation systems. The outside diameter of the tool 10 can be adapted to mate with different styles of cannulated head collets and provide the function desired so along as the axial bore 22 of the tool 10 is constructed in accordance with the invention. The dimensions provided are illustrative of a preferred embodiment only and can be modified as desired both to take into account the individual equipment requirements and the desired depth of cut and plug dimensions required by the surgeon.

Though the invention has been described in connection with hair transplantations systems, it can be appreciated that the surgical cutting tool can also be used in surgical applications such as liposuction and biopsy of tissue along with any other procedure that benefits from the evacuation of tissue via vacuum.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A surgical cutting tool with vacuum clearance capability, comprising a length of cylindrical surgical steel having an axial bore therethrough, a proximal end cutting tip terminating in a cutting edge, and a distal end, the axial bore having a first inside diameter at the cutting edge, a second inside diameter greater than the first inside diameter forming a first relief near the cutting edge, and a third inside diameter greater than the second inside diameter forming a second relief upstream of the first relief, whereby as vacuum is applied at the distal end of the tool tissue plugs cut at the cutting edge pass easily through the first and second reliefs to exit the axial bore.

2. The surgical cutting tool according to claim 1 wherein the length of cylindrical surgical steel is approximately 1.50 inches (3.81 cm).

3. The surgical cutting tool according to claim 2 wherein the first inside diameter at the cutting edge is between 0.0020 inches (0.05 mm) and 0.0600 inches (1.50 mm).

4. The surgical cutting tool according to claim 3 wherein the first inner diameter is 0.0394 inches (1 mm), the second inner diameter is approximately 0.043 inches (1.1 mm), and the third inside diameter is 0.062 inches (1.57 mm).

5. The surgical cutting tool according to claim 4 wherein the first relief is about 0.07 inches (1.7 mm) from the cutting edge.

6. The surgical cutting tool according to claim 5 wherein the second relief is about 0.3 inches (7.3 mm) from the cutting edge.

7. The surgical cutting tool according to claim 1 wherein the outer surface of the cutting tip is angled approximately 20 degrees toward the longitudinal axis of the tool.

8. The surgical cutting tool according to claim 7, the length of cylindrical surgical steel having a reduced outside diameter area from the cutting tip toward the distal end of a length corresponding to a desired depth of punch.

9. The surgical cutting tool according to claim 8, wherein the first relief is at the point of angle of the cutting tip and wherein the second relief is distal to the reduced outside diameter area.

10. A method for making the surgical cutting tool of claim 1, comprising the steps of:
    (a) cutting a piece of cylindrical surgical steel to a desired length to obtain a blank;
    (b) making a drill hole at one end (now the proximal end) of the blank to form the cutting edge;
    (c) drilling open the other end (now the distal end) of the blank along its entire longitudinal axis with a first bit so as to create the axial bore therethrough;
    (d) making a first step-back cut from the distal end toward the proximal end with a second bit having a diameter greater than the first bit to form the first relief; and
    (e) making a second step-back cut from the distal end toward the proximal end with a third bit having a diameter greater than the second bit to form the second relief.

11. The method according to claim 10 further comprising grinding a cutting tip onto the proximal end.

12. The method according to claim 11 further comprising polishing the axial bore to an 8–10 micro finish.

* * * * *